(12) United States Patent
Hatanaka et al.

(10) Patent No.: US 8,175,820 B2
(45) Date of Patent: May 8, 2012

(54) DEFECT INSPECTION APPARATUS AND DEFECT INSPECTION METHOD

(75) Inventors: Hiroaki Hatanaka, Yokohama (JP); Nobukazu Ido, Chigasaki (JP); Minoru Tagami, Yokosuka (JP)

(73) Assignee: IHI Corporation (JP)

( * ) Notice: Subject to any disclaimer, the term of this patent is extended or adjusted under 35 U.S.C. 154(b) by 599 days.

(21) Appl. No.: 12/294,076

(22) PCT Filed: Mar. 24, 2006

(86) PCT No.: PCT/JP2006/305978
§ 371 (c)(1),
(2), (4) Date: Sep. 23, 2008

(87) PCT Pub. No.: WO2007/110900
PCT Pub. Date: Oct. 4, 2007

(65) Prior Publication Data
US 2009/0105967 A1  Apr. 23, 2009

(51) Int. Cl.
 *G01B 11/22* (2006.01)
 *G01B 11/02* (2006.01)
 *G01B 11/06* (2006.01)
 *G01B 15/02* (2006.01)
(52) U.S. Cl. ............ 702/39; 702/35; 702/36; 702/40
(58) Field of Classification Search .......... 702/33, 702/39, 48, 51, 179, 182, 183; 73/40.5, 582, 73/592, 597; 356/237.2
See application file for complete search history.

(56) References Cited

U.S. PATENT DOCUMENTS

| 5,408,881 A | * | 4/1995 | Piche et al. ............ 73/582 |
| 5,714,688 A | * | 2/1998 | Buttram et al. ......... 73/597 |
| 6,220,098 B1 | * | 4/2001 | Johnson et al. ......... 73/592 |

(Continued)

FOREIGN PATENT DOCUMENTS

JP  53-27478 A  3/1978

(Continued)

OTHER PUBLICATIONS

International Search Report and Written Opinion dated Jun. 27, 2006, issued in corresponding International Application No. PCT/JP2006/305978.

*Primary Examiner* — Michael Nghiem
*Assistant Examiner* — Felix Suarez
(74) *Attorney, Agent, or Firm* — Ostrolenk Faber LLP (57) ABSTRACT

An object of the present invention is to quantitatively evaluate a distribution of defects which are generated within an inspection material. In order to achieve this object, the present invention provides a defect inspection apparatus comprising: an ultrasonic wave probe; an ultrasonic wave transmitting and receiving device that irradiates ultrasonic waves via the ultrasonic wave probe onto a surface of an inspection material on which a predetermined propagation medium has been provided, and that also receives as noise signals ultrasonic waves that have been scattered by defects present in the interior of the inspection material; a frequency spectrum calculation device that performs time division on the noise signals so as to divide them into time widths that correspond to positions in the depth direction of the inspection material, and calculates a frequency spectrum for each one of the time-divided noise signals; and a defect distribution detection device that, based on the frequency spectrums, calculates values showing a level of defect progression corresponding to a position in the thickness direction of the inspection material.

12 Claims, 11 Drawing Sheets

U.S. PATENT DOCUMENTS 6,430,988 B1 * 8/2002 Watanabe ................ 73/40.5 A

FOREIGN PATENT DOCUMENTS

| JP | 2-132368 A | 5/1990 |
| --- | --- | --- |
| JP | 3-46070 B2 | 7/1991 |
| JP | 3-257363 A | 11/1991 |
| JP | 5-79829 A | 3/1993 |
| JP | 7-52184 B2 | 6/1995 |
| JP | 2812819 B2 | 8/1998 |
| JP | 2812819 | 10/1998 |
| JP | 2961833 B2 | 8/1999 |
| JP | 2961833 | 10/1999 |
| JP | 2002-31632 A | 1/2002 |
| JP | 2002-139478 A | 5/2002 |
| JP | 2004-245598 A | 9/2004 |

* cited by examiner

(a) INITIAL STATE

(b) AFTER 989 HOURS (LIFESPAN CONSUMPTION RATE 59.8%)

(c) AFTER 1180 HOURS (LIFESPAN CONSUMPTION RATE 71.8%)

(d) AFTER 1510 HOURS (LIFESPAN CONSUMPTION RATE 91.8%)

(e) AFTER 1644 HOURS (LIFESPAN CONSUMPTION RATE 100%)

DEFECT INSPECTION APPARATUS AND DEFECT INSPECTION METHOD

CROSS REFERENCE TO RELATED APPLICATIONS

The present application is a 35 U.S.C. §371 National Phase conversion of PCT/JP2006/305978, filed Mar. 24, 2006. The PCT International Application was published in the Japanese language.

TECHNICAL FIELD

The present invention relates to a defect inspection apparatus and a defect inspection method.

BACKGROUND ART

In metal components that are exposed to high temperatures and high stress such as the rotor blades of boiler pipes and gas turbine engines and the like, there is a possibility that defects such as holes (i.e., voids) and cracks and the like will occur due to creep damage or fatigue failure that is caused by age deterioration. Moreover, in metal components which are used in the pipes of reforming plants that create a gas mixture containing hydrogen by reforming natural gas and the like, there is a possibility of defects such as voids and cracks occurring because of hydrogen corrosion. Inspecting the level to which these defects have progressed and accurately predicting the remaining lifespan of metal components is extremely important for planning the timings of inspections or replacements or the like of the relevant metal components.

For example, in Japanese Patent Publication No. 1646031, a technology is described in which ultrasonic waves are irradiated through the surface of a metal component being inspected, and scattered ultrasonic waves that are generated by defects present inside the metal component are detected as noise signals. This makes it possible to quantitatively inspect the level of defect progression. Moreover, because an intimate relationship exists between the level of defect progression and the remaining lifespan of a metal component, it is possible to predict the remaining lifespan of a metal material from the level of defect progression.

Specifically, a ratio (i.e., a spectrum surface area ratio $S_X/S_O$) of a surface area value $S_O$ of a frequency spectrum that is obtained by performing FFT processing on a noise signal detected when ultrasonic waves are irradiated onto a new metal component having no defects relative to a surface area value $S_X$ of a frequency spectrum that is obtained by performing FFT processing on a noise signal detected when ultrasonic waves are irradiated onto a metal component that has been in operation for a predetermined period of time is determined as the level of defect progression.

Figure 12:
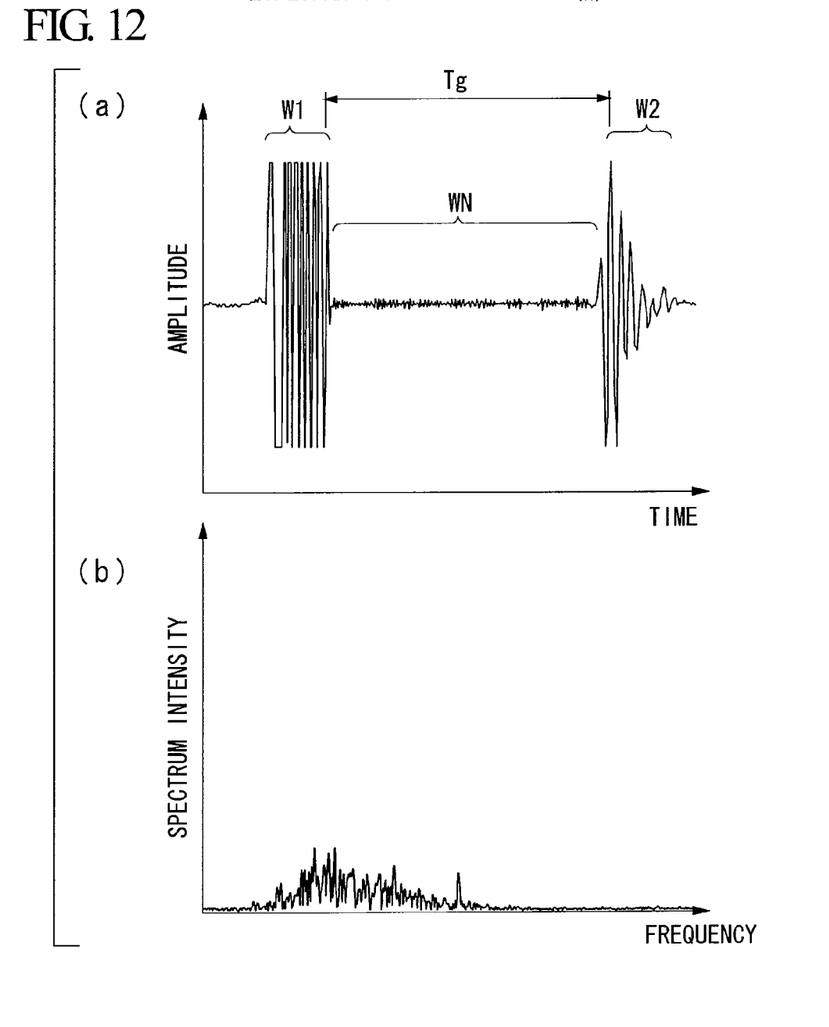
FIG. 12 is a first explanatory view showing a conventional defect detection method.
Figure 13:
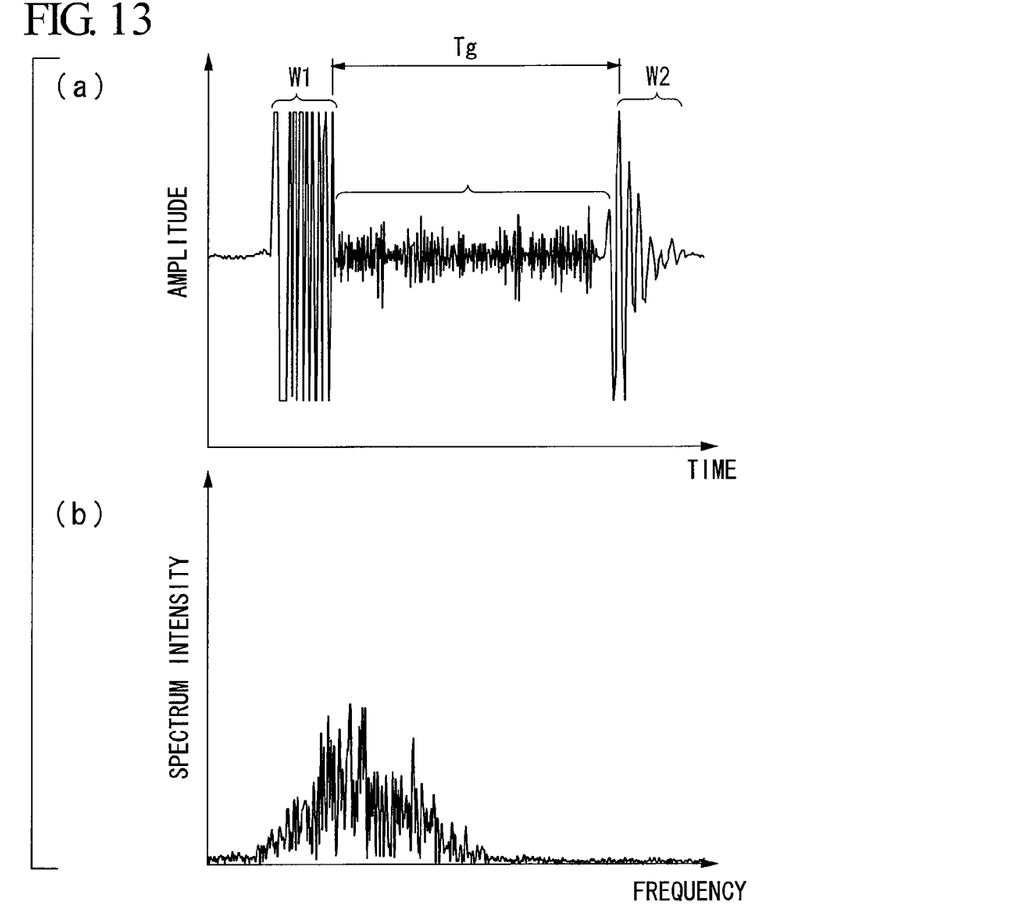
FIG. 13 is a second explanatory view showing a conventional defect detection method.

FIG. 12 (a) shows an example of a noise signal which is detected when ultrasonic waves are irradiated onto a new metal component having no defects. In this drawing, the symbol W1 is irradiated an ultrasonic wave signal, WN is a noise signal, W2 is a bottom surface reflected signal that is obtained when the irradiated ultrasonic wave is reflected by the bottom surface (i.e., the rear surface) of the metal component, and is detected at the front surface thereof. FIG. 12 (b) shows a frequency spectrum which is obtained when the noise signal WN which has been detected in this manner is extracted as a time window corresponding to a time width Tg, and FFT processing is then performed on this extracted signal. FIG. 13 (a) shows an example of the noise signal WN which is detected when ultrasonic waves are irradiated onto a metal component that has been in operation for a predetermined period of time. As is shown in this drawing, when a certain operating time has passed, a large number of defects are generated. As a result, the detected noise signal WN also grows larger. FIG. 13 (b) shows a frequency spectrum which is obtained when the noise signal WN which has been detected in this manner is extracted as a time window corresponding to the time Tg, and FFT processing is then performed on this extracted signal.

Figure 14:
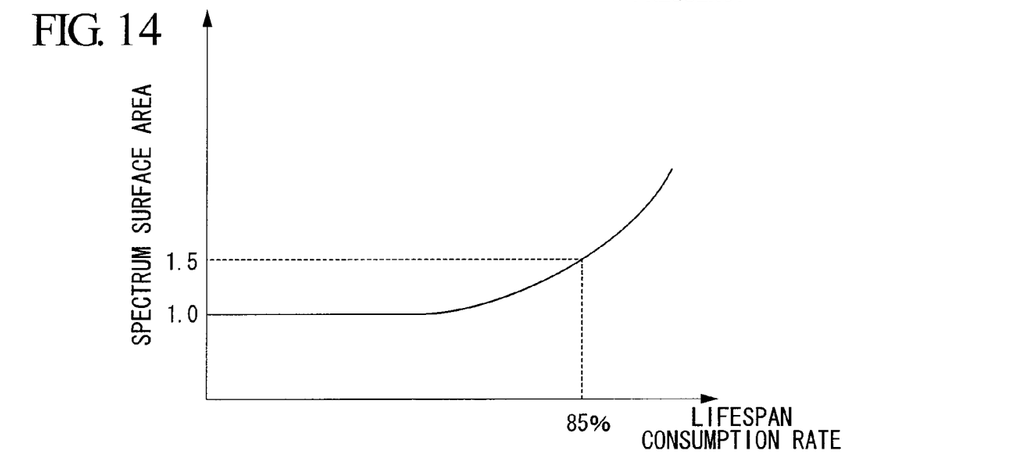
FIG. 14 is a third explanatory view showing a conventional defect detection method.

Namely, a ratio between the surface area value $S_O$ of the frequency spectrum shown in FIG. 12 (b) and the surface area value $S_X$ of the frequency spectrum shown in FIG. 13 (b) is the spectrum surface area ratio $S_X/S_O$. In contrast, FIG. 14 shows an example of a characteristic curve (referred to below as the remaining lifespan curve) that shows a relationship between a spectrum surface area ratio $S_X/S_O$ that has been determined by experiment in advance, and a lifespan consumption rate of a metal component. Here, assuming that the remaining lifespan curve relates to creep damage, for example, then the lifespan consumption rate is a ratio of a time t that has elapsed since the metal component began to operate relative to a creep rupture lifespan time $t_f$. If a spectrum surface area ratio $S_X/S_O$ of 1.5 is obtained for a metal component that has been in operation for a predetermined period of time, then it is found that the lifespan consumption rate of this metal component is approximately 85% based on the aforementioned FIG. 14. Accordingly, the remaining lifespan can be predicted to be 15% of the creep rupture lifespan $t_f$.

Patent document 1: Japanese Patent Publication No. 1646031

DISCLOSURE OF THE INVENTION

Problems to be Solved by the Invention

In the above described conventional technology, it is possible to quantitatively evaluate the level of defect progression, and based on the relationship between the level of defect progression and the lifespan consumption rate of a metal component, it is possible to predict the remaining lifespan of a metal component. However, conventionally, the level of defect progression is quantitatively evaluated over the entire plate thickness direction of a metal component, and in which portion in the plate thickness direction a large defect has been generated has not been evaluated, namely, the defect distribution in the plate thickness direction has not been quantitatively evaluated.

In this manner, the quantitative evaluation of the distribution of defects occurring inside a metal component is extremely important when a process from the occurrence of a defect to the failure of the metal component is being examined.

The present invention was conceived in view of the above described circumstances, and it is an object thereof to quantitatively evaluate the distribution of defects occurring inside a material being inspected.

Means for Solving the Problem

In order to achieve the above described object, a first aspect of the defect inspection apparatus of the present invention includes: an ultrasonic wave probe; an ultrasonic wave transmitting and receiving device that irradiates ultrasonic waves via the ultrasonic wave probe onto a surface of an inspection material on which a predetermined propagation medium has been provided, and that also receives as noise signals ultrasonic waves that have been scattered by defects present in the interior of the inspection material; a frequency spectrum calculation device that performs time division on the noise signals so as to divide them into time widths that correspond to positions in the depth direction of the inspection material, and calculates a frequency spectrum for each one of the time-divided noise signals; and a defect distribution detection device that, based on the frequency spectrums, calculates values showing a level of defect progression corresponding to a position in the thickness direction of the inspection material.

Moreover, according to a second aspect of the defect inspection apparatus of the present invention, in the above described first aspect there is further provided an ultrasonic probe drive device that moves the ultrasonic probe along the surface of the inspection material, and also lowers the ultrasonic probe towards this surface so that the ultrasonic probe comes into contact with the surface at each inspection position on the surface of the inspection material, and for each inspection position, the defect distribution detection device calculates values showing the level of defect progression corresponding to a position in the depth direction of the inspection material, and creates two-dimensional distribution data for the values which show the level of defect progression.

Moreover, according to a third aspect of the defect inspection apparatus of the present invention, in the above described second aspect the ultrasonic probe is rotated in an in-plane direction of the inspection surface when it is being brought into contact via the propagation medium with the surface of the inspection material.

Moreover, according to a fourth aspect of the defect inspection apparatus of the present invention, in the above described first aspect the ultrasonic wave transmitting and receiving device receives via the ultrasonic wave probe ultrasonic waves that have been reflected by the bottom surface of the inspection material as bottom surface reflected signals, and there is further provided a determination device that determines whether or not the ultrasonic waves are being correctly irradiated onto the inspection material based on the strength of the bottom surface reflected signals.

Moreover, according to a fifth aspect of the defect inspection apparatus of the present invention, in the above described first aspect the frequency of the ultrasonic waves is set in accordance with the time widths which are obtained as a result of time division being performed on the noise signals.

Moreover, according to a sixth aspect of the defect inspection apparatus of the present invention, in the above described first aspect there is further provided a breakage lifespan determination device that determines a lifespan before breakage of the inspection material based on the value showing the level of defect progression.

In a first aspect of the defect inspection method of the present invention: ultrasonic waves are irradiated onto a surface of an inspection material via a predetermined propagation medium, and ultrasonic waves that have been scattered by defects present in the interior of the inspection material are detected as noise signals; time division is performed on the detected noise signals so as to divide them into time widths that correspond to positions in the depth direction of the inspection material; a frequency spectrum is calculated for each one of the time-divided noise signals; and based on the frequency spectrums, values showing a level of defect progression corresponding to a position in the thickness direction of the inspection material are calculated.

Moreover, according to a second aspect of the defect inspection method of the present invention, in the above described first aspect ultrasonic waves are irradiated onto each inspection position on the surface of the inspection material; for each of the inspection positions, values showing the level of defect progression corresponding to a position in the depth direction of the inspection material are calculated; and two-dimensional distribution data is created for the values which show the level of defect progression Moreover, according to a third aspect of the defect inspection method of the present invention, in the above described first aspect the propagation medium is oil having a density of 1 (g/cm$^3$) or less and a kinematic viscosity of 100 (mm$^2$/s) or less.

Moreover, according to a fourth aspect of the defect inspection method of the present invention, in the above described first aspect the ultrasonic waves that have been reflected by the bottom surface of the inspection material are detected as bottom surface reflected signals, and whether or not the ultrasonic waves are being correctly irradiated onto the inspection material is determined based on the strength of the bottom surface reflected signals.

Moreover, according to a fifth aspect of the defect inspection method of the present invention, in the above described first aspect the frequency of the ultrasonic waves is set in accordance with the time widths which are obtained as a result of time division being performed on the noise signals.

Moreover, according to a sixth aspect of the defect inspection method of the present invention, in the above described first aspect a lifespan before breakage of the inspection material is determined based on the value showing the level of defect progression.

Effects of the Invention

According to the present invention, because ultrasonic waves are irradiated onto a surface of an inspection material via a predetermined propagation medium, and ultrasonic waves that have been scattered by defects present in the interior of the inspection material are detected as noise signals, and because time division is performed on the detected noise signals so as to divide them into time widths that correspond to positions in the depth direction of the inspection material, and because a frequency spectrum is calculated for each one of the time-divided noise signals, and because, based on the frequency spectrums, values showing a level of defect progression corresponding to a position in the thickness direction of the inspection material are calculated, it is possible to quantitatively the defect distribution in the depth direction of an inspection material.

DESCRIPTION OF THE REFERENCE NUMERALS

1 . . . Ultrasonic wave probe, 2 . . . Probe drive unit, 3 . . . Ultrasonic wave transmitting and receiving unit, 4 . . . A/D converter, 5 . . . Frequency spectrum calculation unit, 6 . . . Defect distribution detection unit, 7 . . . Image processing unit, 8 . . . Control unit, 9 . . . Storage unit, 10 . . . . Display unit
Best Embodiments for Implementing the Invention An embodiment of the present invention will now be described with reference made to the drawings.

Figure 1:
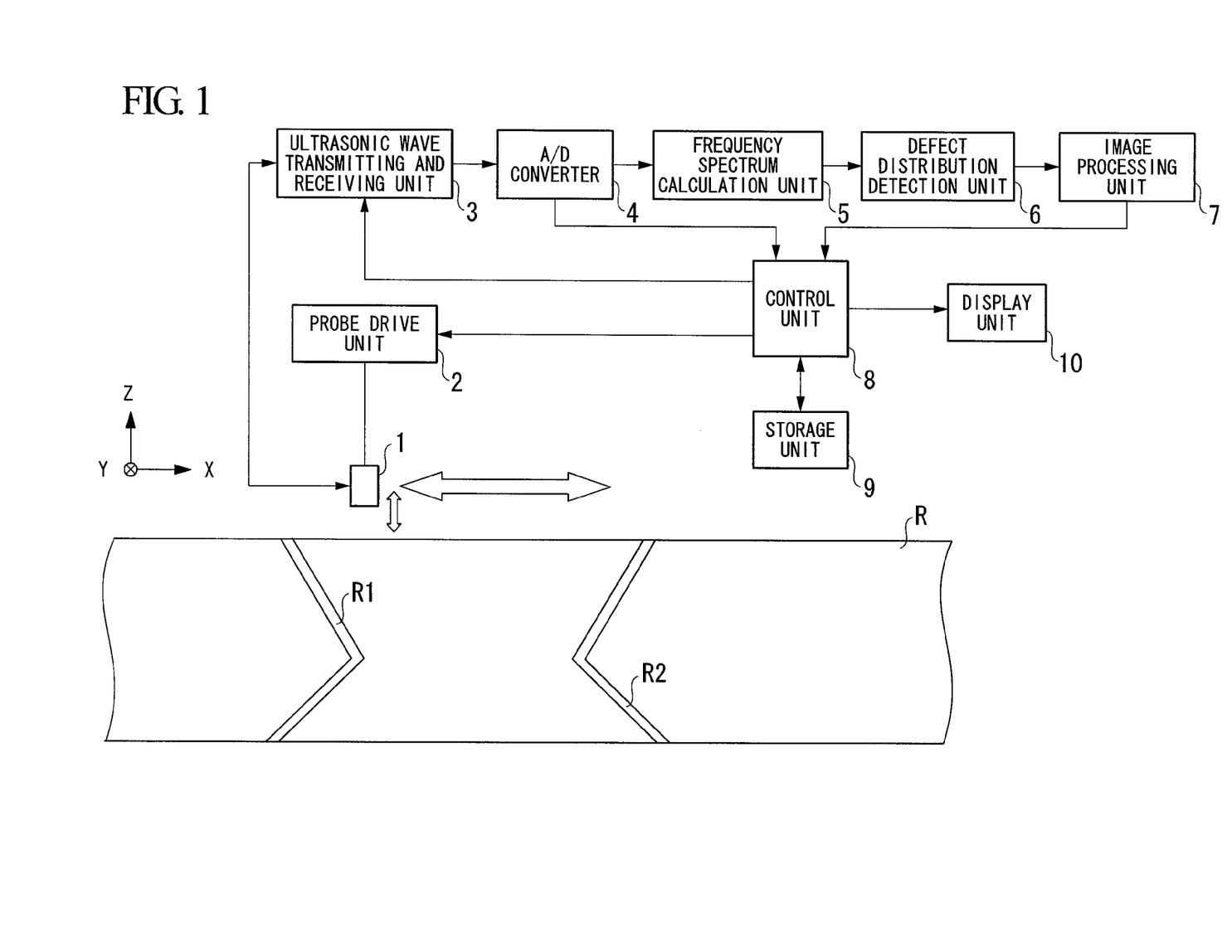
FIG. 1 is a block diagram showing the structure of a defect inspection apparatus according to an embodiment of the present invention.

FIG. 1 is a structural block diagram of a defect inspection apparatus according to the embodiment of the present invention. Incidentally, the defect inspection apparatus quantitatively evaluates a distribution of defects which are caused by creep damage within a metal component (inspection material R) including weld portions R1 and R2.

As is shown in FIG. 1, this defect inspection apparatus is formed by an ultrasonic wave probe 1, a probe drive unit 2, an ultrasonic wave transmitting and receiving unit 3, an A/D converter 4, a frequency spectrum calculation unit 5, a defect distribution detection unit 6, an image processing unit 7, a control unit 8, a storage unit 9, and a display unit 10.

The ultrasonic wave probe 1 irradiates ultrasonic waves having a frequency bandwidth of 4 to 20 MHz which are input from the ultrasonic wave transmitting and receiving unit 3 onto a surface of an inspection material R via a predetermined contact medium. The ultrasonic wave probe 1 also receives ultrasonic waves (i.e., scattered waves) that have been scattered by defects such as voids and cracks present inside the inspection material R, and ultrasonic waves (i.e., bottom surface reflected waves) which are reflected by a bottom surface (i.e., a rear surface) of the inspection material R. This ultrasonic wave probe 1 is also mechanically connected to the probe drive unit 2, and is moved by the probe drive unit 2 in the X axial direction, namely, along the surface of the inspection material R, and is moved up and down in the Z axial direction, namely, in a perpendicular direction relative to the surface of the inspection material R.

Figure 2:
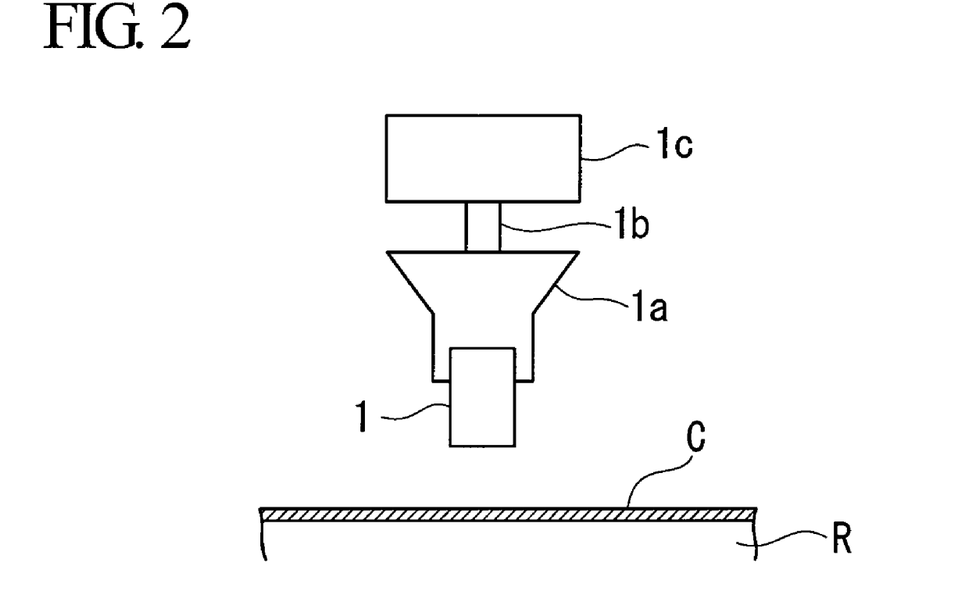
FIG. 2 is a detailed drawing showing an area peripheral to an ultrasonic wave probe 1 according to an embodiment of the present invention.

FIG. 2 shows in detail the structure of an area around the above described ultrasonic wave probe 1. As is shown in this drawing, the ultrasonic wave probe 1 is gripped by means of a probe holder 1a, and this probe holder 1a is rotatably connected via a connecting bolt 1b to a scanning unit connection jig 1c. The scanning unit connection jig 1c is connected to a portion (not shown) of the probe drive unit 2 that is able to move in the X and Z axial direction. A contact medium C is coated in advance to a predetermined thickness on the surface of the inspection material R. A material having low viscosity is preferably used for the contact medium C and, for example, oil having a density of 1 (g/cm$^3$) or less and a kinematic viscosity of 100 (mm$^2$/s) or less is preferably used.

Returning to FIG. 1, under the control of the control unit 8, the probe drive unit 2 causes the ultrasonic wave probe 1 (specifically, including the probe holder 1a, the connecting bolt 1b, and the scanning unit connection jig 1c) to move in the X axial direction, and to move up and down in the Z axial direction. Under the control of the control unit 8, the ultrasonic wave transmitting and receiving unit 3 generates ultrasonic waves having a frequency bandwidth of 4 to 20 MHz, and outputs these to the ultrasonic wave probe 1 at a predetermined timing. The ultrasonic wave transmitting and receiving unit 3 also detects scattered waves and bottom surface reflected waves received by the ultrasonic wave probe 1, and outputs to the A/D converter 4 irradiation signals W1 that show the irradiated ultrasonic waves, noise signals WN that show the scattered waves, and bottom surface reflected signals W2 that show the bottom surface reflected waves.

The A/D converter 4 converts the irradiation signals W1, the noise signals WN, and the bottom surface reflected signals W2 which are analog signals into digital signals, and outputs these to the frequency spectrum calculation unit 5. The A/D converter 4 also outputs the digitally converted bottom surface reflected signals W2 to the control unit 8. The frequency spectrum calculation unit 5 performs FFT processing on the noise signals WN based on the irradiation signals W1, the noise signals WN, and the bottom surface reflected signals W2 that have been converted into digital signals by the A/D converter 4, and outputs to the defect distribution detection unit 6 information which shows the frequency spectrum obtained from this FFT processing. Note that the frequency spectrum calculation unit 5 calculates a frequency spectrum by dividing a time width Tg from when the irradiation signal W1 is irradiated until the bottom surface reflected signal W2 is received into a plurality of time widths Tg1 to Tgn, and then performing FFT processing on each one of noise signals WN1 to WNn that are extracted in time windows which correspond to the respective divided time widths Tg1 to Tgn (this process is described in more detail below).

The defect distribution detection unit 6 calculates surface area values ($S_x1$ to $S_xn$) of the frequency spectrums of each one of the noise signals WN1 to WNn based on the information showing the frequency spectrum which has been input from the frequency spectrum calculation unit 5, and calculates a ratio (i.e., a spectrum surface area ratio) between the surface area values ($S_x1$ to $S_xn$) and the surface area value $S_O$ of the frequency spectrum of the noise signal in an inspection material having no defects which has been determined by experiment in advance as a value showing the level of defect progression, and outputs a spectrum surface area ratio for each one of the noise signals WN1 to WNn to the image processing unit 7.

The image processing unit 7 generates image data showing a relationship between the positions in the depth direction of the inspection material R which correspond to the noise signals WN1 to WNn (namely, which correspond to the respective divided time widths Tg1 to Tgn) and the spectrum surface area ratios based on the spectrum surface area ratios of each of the noise signals WN1 to WNn which have been input from the defect distribution calculation unit 6, and then outputs this data to the control unit 8. Note that because the ultrasonic wave probe 1 is moved in the X axial direction by the probe drive unit 2 (described below in more detail), the image processing unit 7 generates image data showing the distribution of a two-dimensional spectrum surface ratio for the depth direction and the X axial direction of the inspection material R.

The control unit 8 controls the overall operation of this defect inspection apparatus based on a control program which is stored in the storage unit 9, and controls the movement in the X axial direction and the up-down movement in the Z axial direction of the ultrasonic wave probe 1 by the probe drive unit 2, and also controls the irradiation and the like of ultrasonic waves by the ultrasonic wave transmitting and receiving unit 3. The control unit 8 also causes image data which is input from the image processing unit 7 to be stored in the storage unit 9, and generates display signals that are used to display the image data and outputs these to the display unit 10. The control unit 8 also performs coupling checks (described below in more detail) based on the bottom surface reflected signals W2 which are input from the A/D converter 4. The storage unit 9 stores the control program, image data, and other various types of data that are used by the above described control unit 8. The display unit 10 displays an image showing the distribution of the two-dimensional spectrum surface ratio for the depth direction and the X axial direction of the inspection material R based on display signals input from the control unit 8.

Next, a description will be given of a defect inspection operation of this defect inspection apparatus having the above described structure.

[Coupling Check Operation]

Firstly, a coupling check operation will be described. A coupling check is a process to determine whether or not ultrasonic waves are being irradiated correctly when the ultrasonic wave probe 1 is brought into contact with the surface of the inspection material R on which the contact medium C has been coated in advance in order to irradiate ultrasonic waves.

Figure 3:
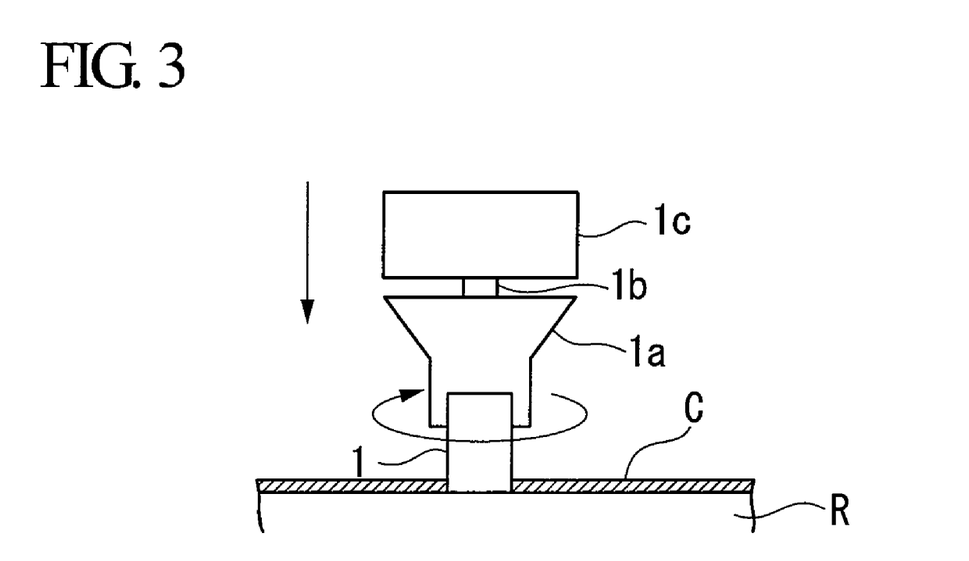
FIG. 3 is a detailed drawing showing a state of contact of the ultrasonic wave probe 1 according to an embodiment of the present invention.

Assuming that the ultrasonic wave probe 1 is in a position such as that shown in FIG. 2, namely, is in an initial state, the control unit 8 controls the probe drive unit 2 such that the ultrasonic wave probe 1 is lowered in the Z axial direction so as to come into contact with the surface of the inspection material R via the contact medium C. At this time, after the ultrasonic wave probe 1 has come into contact with the surface of the inspection material R, it is further lowered in the Z axial direction by a particular fixed distance. By performing this action, as is shown in FIG. 3, because force is applied in a direction in which the gap between the probe holder 1a and the scanning unit connection jig 1c becomes smaller, the connecting bolt 1b rotates as a single body together with the probe holder 1a. As a result, the contact medium C is made to properly stick to the contact surface of the ultrasonic wave probe 1, and air between the ultrasonic wave probe 1 and the inspection material R can be removed so that ultrasonic waves can be correctly irradiated.

Note that the distance by which the ultrasonic wave probe 1 is further lowered after it has come into contact with the surface of the inspection material R is desirably set at a distance which is reached by rotating the ultrasonic wave probe 1 approximately 90°. It is also desirable for there to be provided a sensor that detects the fact that the ultrasonic wave probe 1 has come into contact with the surface of the inspection material R, as well as a mechanism that restores the connecting bolt 1b and the probe holder 1a to their original states when the ultrasonic wave probe 1 has been moved away from the surface of the inspection material R.

Furthermore, in the present embodiment, oil having a density of 1 (g/cm$^3$) or less and a kinematic viscosity of 100 (mm$^2$/s) or less is preferably used for the contact medium C in order to allow the ultrasonic waves to propagate. Generally, in a nondestructive inspection in which ultrasonic waves are used, a material having a comparatively high viscosity such as glycerin paste has been used as the contact medium. This has been for the reason that because the propagation efficiency of the ultrasonic waves improves as the density and the viscosity of the contact medium increase, it becomes possible to maintain a high irradiation intensity of the ultrasonic waves onto the inspection material, which makes it possible to reduce the effects of noise from external disturbances.

However, when this type of contact medium having a high density and a high viscosity is used, it is easy for the distance between the ultrasonic wave probe 1 and the surface of the inspection material R to be irregular depending on the position where the ultrasonic waves are irradiated. Namely, depending on the position where the ultrasonic waves are irradiated, the irradiation intensity varies considerably, so that it becomes difficult to accurately detect any defect. Moreover, because the present defect detection apparatus quantitatively detects minute defects generated by creep damage, it is necessary to keep the distance between the ultrasonic probe 1 and the surface of the inspection material R to the minimum and to also keep this distance fixed. Accordingly, by using the aforementioned type of oil having a low density and a low viscosity, it is possible to form a uniform contact medium having a small film thickness, and to accurately detect defects.

As has been described above, when the ultrasonic wave probe 1 is brought into contact with the surface of an inspection material, the control unit 8 controls the ultrasonic wave transmitting and receiving unit 3 such that ultrasonic waves are irradiated into the interior of the inspection material R via the ultrasonic wave probe 1. The irradiated ultrasonic waves are scattered by defects present in the interior of the inspection material R, and scattered waves that are generated by this scattering are received by the ultrasonic wave probe 1. In addition, the ultrasonic waves that are reflected by the bottom surface (i.e., the rear surface) of the inspection material R (i.e., bottom surface reflected waves) are also received by the ultrasonic wave probe 1.

Figure 4:
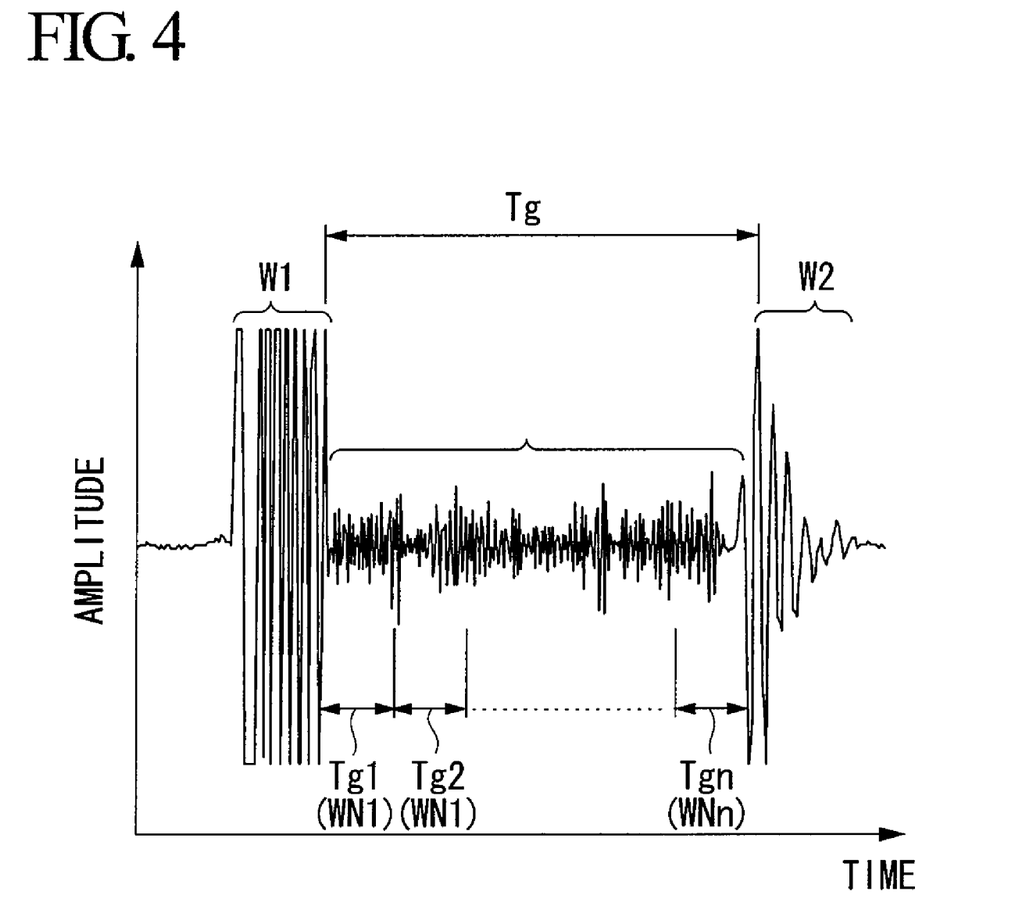
FIG. 4 is an explanatory view showing a method of detecting defect distribution according to an embodiment of the present invention.

The ultrasonic wave transmitting and receiving unit 3 detects the scattered waves and the bottom surface reflected waves received by the ultrasonic wave probe 1, and outputs to the A/D converter 4 irradiation signals W1 that show the irradiated ultrasonic waves, noise signals WN that show the scattered waves, and bottom surface reflected signals W2 that show the bottom surface reflected waves. These irradiation signals W1, noise signals WN, and bottom surface reflected signals W2 are shown in FIG. 4. Here, if the ultrasonic waves are not irradiated correctly, the amplitude of the bottom surface reflected signals W2 is reduced. Accordingly, if the amplitude of the bottom surface reflected signals W2 is smaller than a predetermined threshold value, it can be determined that the ultrasonic waves are not being irradiated correctly.

Specifically, the A/D converter 4 outputs to the control unit 8 the digitally converted bottom surface reflected signals W2. The control unit 8 compares the amplitude of the bottom surface reflected signal W2 with a predetermined threshold value and, if the amplitude is less than the threshold value, determines that the ultrasonic waves are not being correctly irradiated. This determination result is then displayed on the display unit 10, and a user is notified that a coupling error has occurred. The control unit 8 then controls the probe drive unit 2 so that the ultrasonic probe 1 is moved in the X axial direction, and then once again detects the bottom surface reflected signals W2. Note that when the ultrasonic wave probe 1 is being moved in the X axial direction, it is desirable for the ultrasonic wave probe 1 to first be temporarily lifted in the Z axial direction from the surface of the inspection material R and then moved.

As has been described above, the control unit 8 compares the amplitude of the bottom surface reflected signal W2 with a predetermined threshold value, and if the amplitude is equal to or more than the threshold value, determines that the ultrasonic waves are being correctly irradiated and commences the defect scan described below.

[Defect Scan]

When the coupling check is ended (at this time, the ultrasonic wave probe 1 is in contact with the surface of the inspection material R via the contact medium C), the control unit 8 controls the ultrasonic wave transmitting and receiving unit 3 so that ultrasonic waves are irradiated into the interior of the inspection material R from the ultrasonic wave probe 1. The ultrasonic wave transmitting and receiving unit 3 detects scattered waves and bottom surface reflected waves received by the ultrasonic wave probe 1, and outputs to the A/D converter 4 the irradiation signals W1 that show the irradiated ultrasonic waves, the noise signals WN that show the scattered waves, and the bottom surface reflected signals W2 that show the bottom surface reflected waves (see FIG. 4). The A/D converter 4 converts the irradiation signals W1, the noise signals WN, and the bottom surface reflected signals W2 which are analog signals into digital signals, and outputs these to the frequency spectrum calculation unit 5.

The frequency spectrum calculation unit 5 performs FFT processing on the noise signals WN based on the irradiation signals W1, the noise signals WN, and the bottom surface reflected signals W2 that have been converted into digital signals by the A/D converter 4, and outputs to the defect distribution detection unit 6 information which shows the frequency spectrum obtained from this FFT processing. More specifically, the frequency spectrum calculation unit 5 calculates a frequency spectrum by dividing a time width Tg from when the irradiation signal W1 is irradiated until the bottom surface reflected signal W2 is received (see FIG. 4) into a plurality of time widths Tg1 to Tgn, and then performing FFT processing on each one of noise signals WN1 to WNn that are extracted in time windows which correspond to the respective divided time widths Tg1 to Tgn.

Each of these divided time widths Tg1 to Tgn corresponds to a position in the depth direction of the inspection material R. For example, when detecting defects at a pitch of 1 mm in the depth direction of the inspection material R, then assuming a propagation speed of 5.95 (mm/μs) for the ultrasonic waves inside the inspection material R (i.e., the longitudinal wave acoustic velocity in a typical steel material), this 1 mm distance can be converted into a time width using the following formula.

$$1 \text{ (mm)}/5.95 \text{ (mm/μs)} \times 2 = 0.34 \text{ (μs)} \quad (1)$$

Namely, the respective time widths Tg1 to Tgn are obtained by dividing the time width Tg equally into 0.34 (μs) units. In this manner, by dividing the time width Tg into the respective time widths Tg1 to Tgn, and then performing FFT processing on each of the noise signals WN1 to WNn that are extracted in time windows that correspond to the respective time widths Tg1 to Tgn, it is possible to obtain a frequency spectrum such as that shown in FIG. 13 (b) at each 1 mm pitch in the thickness direction of the inspection material R.

The defect distribution detection unit 6 calculates surface area values ($S_X1$ to $S_Xn$) of the frequency spectrums for each one of the divided noise signals WN1 to WNn based on the information showing the frequency spectrum which has been input from the frequency spectrum calculation unit 5, and calculates a ratio (i.e., a spectrum surface area ratio) between the surface area values ($S_X1$ to $S_Xn$) and the surface area value $S_O$ of the frequency spectrum of the noise signal in an inspection material having no defects which has been determined by experiment in advance, and outputs spectrum surface area ratios P1 to Pn for each one of the noise signals WN1 to WNn to the image processing unit 7. These spectrum surface area ratios are values that show the level of defect progression.

The image processing unit 7 generates image data showing a relationship between the positions in the depth direction of the inspection material R which correspond to the respective noise signals WN1 to WNn (namely, which correspond to the respective divided time widths Tg1 to Tgn) and the spectrum surface area ratios P1 to Pn based on these spectrum surface area ratios P1 to Pn. Note that, at this point, because the image data shows a relationship between the spectrum surface area ratios P1 to Pn and the position in the depth direction of the inspection material R at an inspection position at a coordinate located on the X axis, the image data is one-dimensional data.

Figure 5:
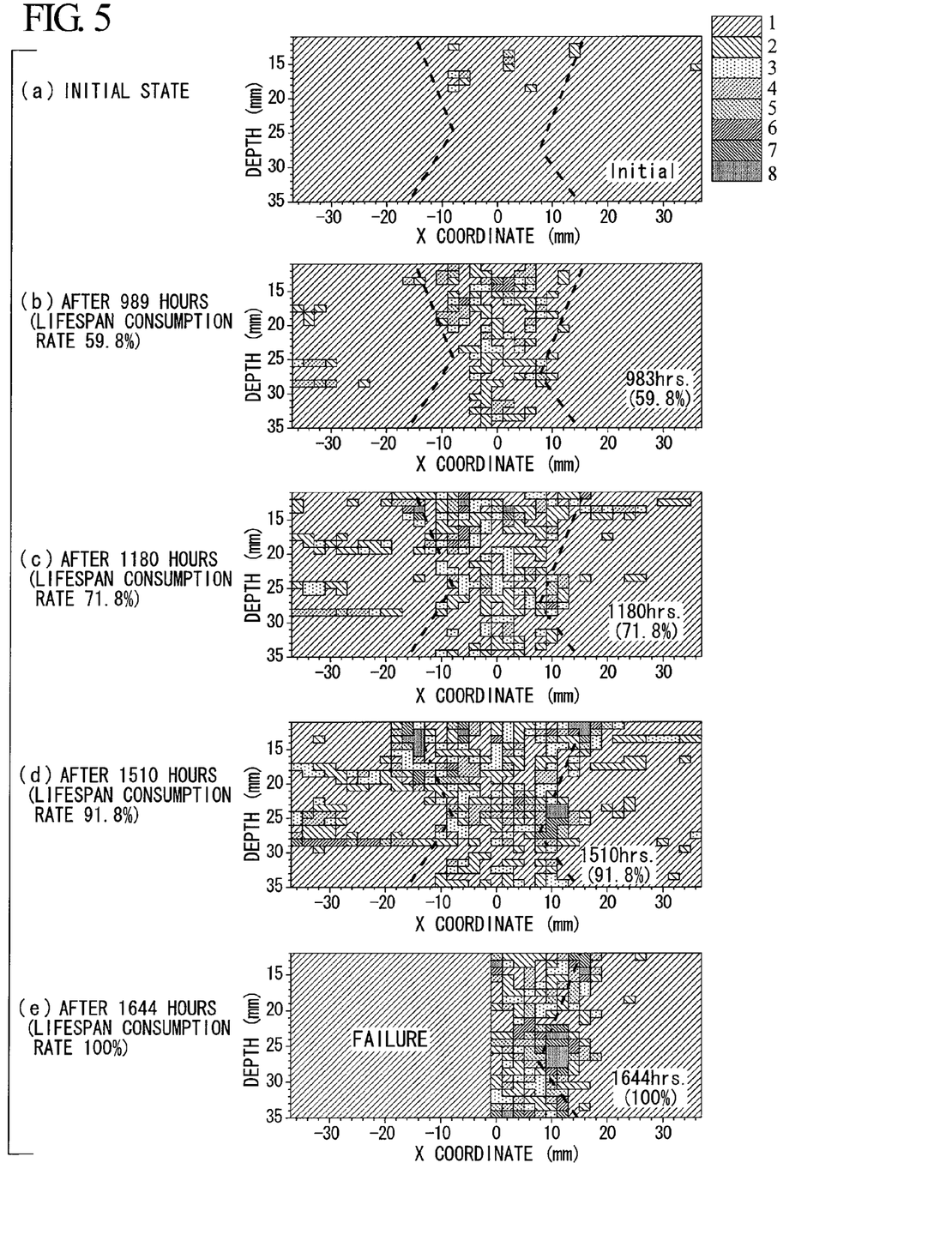
FIG. 5 is a typical view of a defect distribution detected by means of a defect inspection apparatus according to an embodiment of the present invention.

Next, the control unit 8 controls the probe drive unit 2 so that the ultrasonic probe 1 is moved a fixed distance (for example, several millimeters) in the X axial direction (i.e., in the scanning direction), and a coupling check is performed. After this coupling check, the relationship between the spectrum surface area ratios P1 to Pn and the position in the depth direction of the inspection material R at a coordinate on the X axis is once again detected, and image data is generated. By repeating this type of operation, as is shown in FIG. 5, it is possible to obtain image data showing the distribution of a spectrum surface area ratio whose vertical axis is the position in the depth direction of the inspection material R and whose horizontal axis is the X axial coordinate, namely, to obtain a defect distribution. The control unit 8 generates display signals that are used to display the above described image data and outputs these to the display unit 10. Based on these display signals, the display unit 10 displays an image showing the distribution of a two-dimensional spectrum surface ratio for the X axial direction and the depth direction of the inspection material R (i.e., the distribution of defects).

FIG. 5 shows the defect distribution from the point in time when the inspection material R began operating (i.e., from an initial state) until creep damage (i.e., until the lifespan consumption rate was 100%). A pattern is formed that shows the larger the value of the spectrum surface area (namely, the greater the level of defect progression), the higher the numerical value. Here, numerical values from 1 (a low level of defect progression) to 8 (a high level of defect progression) are allocated to show the level of defect progression.

As is shown in FIG. 5, it is possible to quantitatively evaluate what size of defect has occurred, and in what location inside the inspection material R a defect has occurred when a particular time has elapsed since the inspection material R started operating. It can be seen from FIG. 5 that, in conjunction with the passage of time (i.e., with the progression of creep damage), a large number of defects are generated in the area around weld portions R1 and R2.

Figure 6:
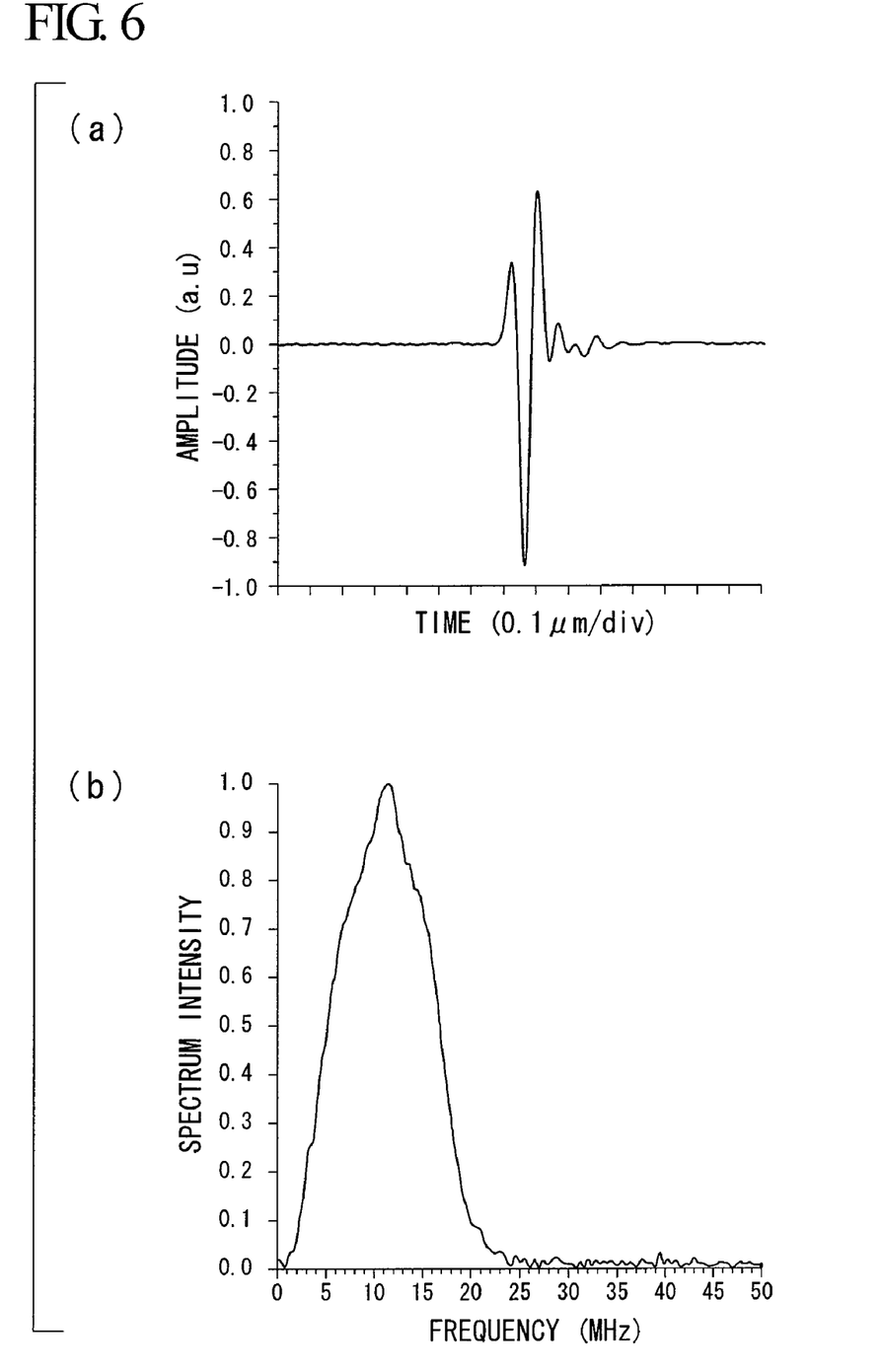
FIG. 6 is an explanatory view showing characteristics of the ultrasonic waves used by the defect inspection apparatus according to an embodiment of the present invention.

In the present embodiment, ultrasonic waves having amplitude characteristics such as those shown in FIG. 6 (a) and frequency characteristics such as those shown in FIG. 6 (b) are used. As is shown in FIG. 6 (b), these ultrasonic waves have a central frequency of 12 (MHz), and frequencies thereof that are reduced by 20 (dB) from the peak intensity are 4 and 20 (MHz), namely, they have a frequency bandwidth of 4 to 20 (MHz). The reason why such ultrasonic waves are used is described below.

Firstly, as is described above, in order to obtain a spectrum surface area ratio at 1 mm intervals in the thickness direction of the inspection material R, it is necessary to divide the time width Tg equally into 0.34 (μs). Because the minimum frequency component that can be contained within this 0.34 (μs) time width is 1/0.34 (μs)=2.95 (MHz), any analysis of frequency components below this 2.95 (MHz) is liable to contain considerable errors. Accordingly, it is essential to have a frequency band larger than 2.95 (MHz). This is the first reason.

The second reason will be described using the results of an experiment in which the two-dimensional defect distribution was evaluated in the X axial direction and the thickness direction of the inspection material R when the frequency band of the ultrasonic waves was actually changed. Note that, in this experiment, the distribution of defects that were generated as a result of creep damage was evaluated in areas around weld portions in an inspection material R such as that shown in FIG. 1.

Figure 7:
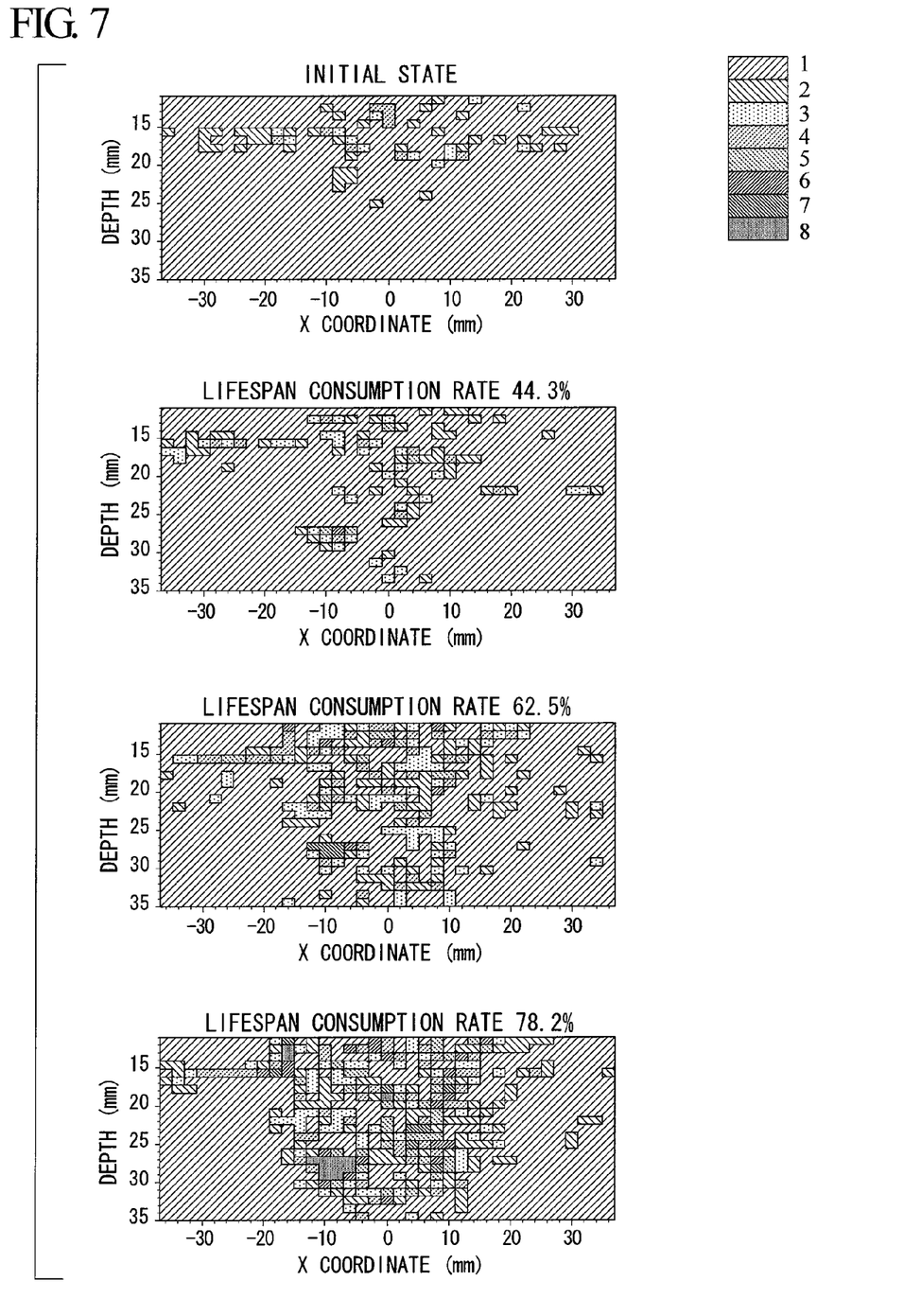
FIG. 7 is a typical view of a defect distribution detected when ultrasonic waves having a frequency bandwidth of 4 to 8 (MHz) are used in the defect inspection apparatus according to an embodiment of the present invention.
Figure 8:
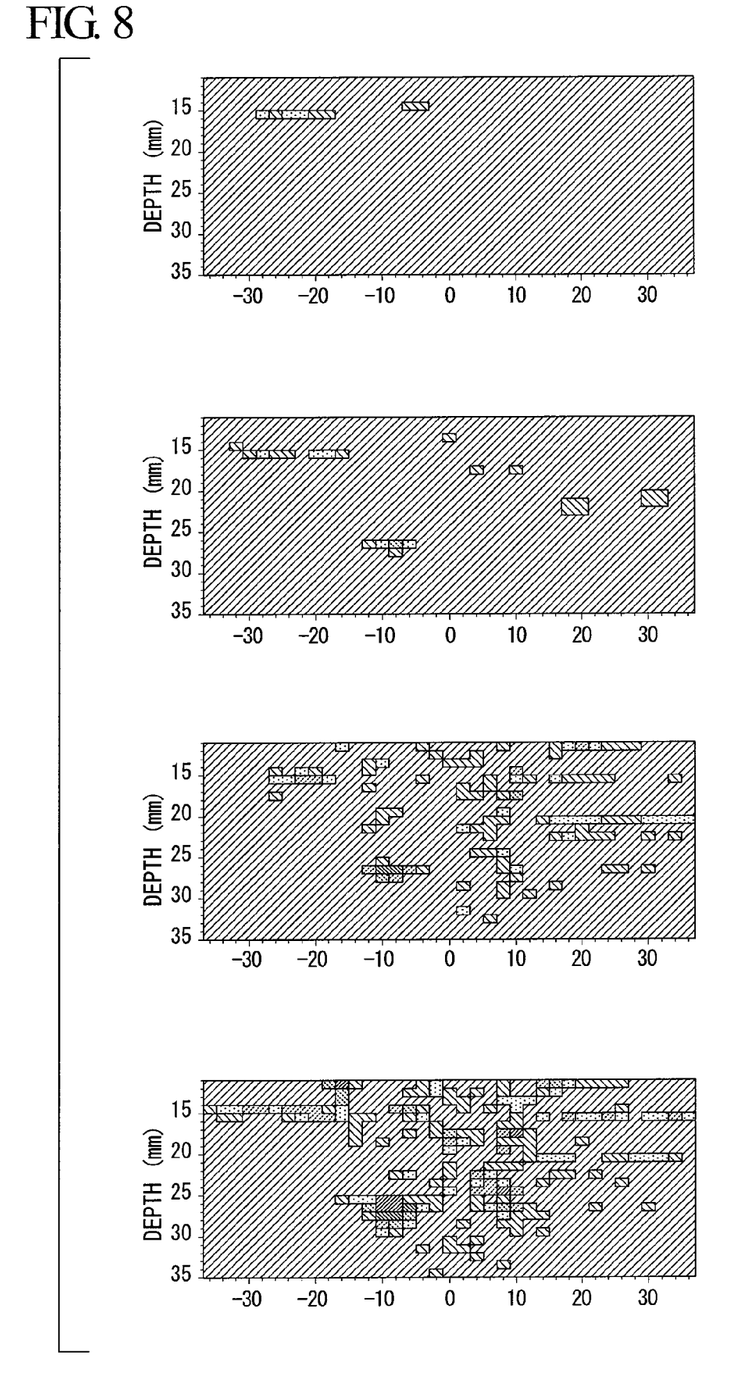
FIG. 8 is a typical view of a defect distribution detected when ultrasonic waves having a frequency bandwidth of 4 to 20 (MHz) are used in the defect inspection apparatus according to an embodiment of the present invention.
Figure 9:
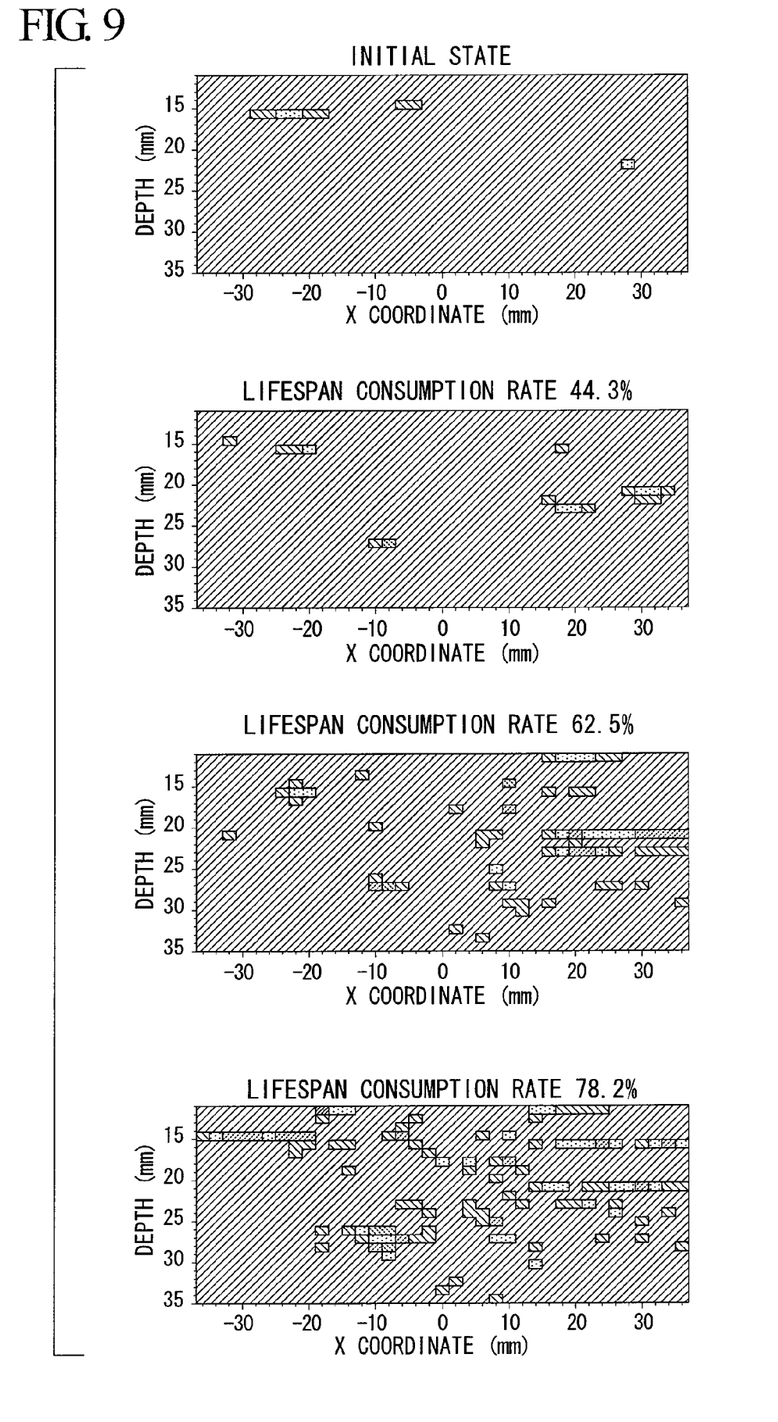
FIG. 9 is a typical view of a defect distribution detected when ultrasonic waves having a frequency bandwidth of 10 to 20 (MHz) are used in the defect inspection apparatus according to an embodiment of the present invention.
Figure 10:
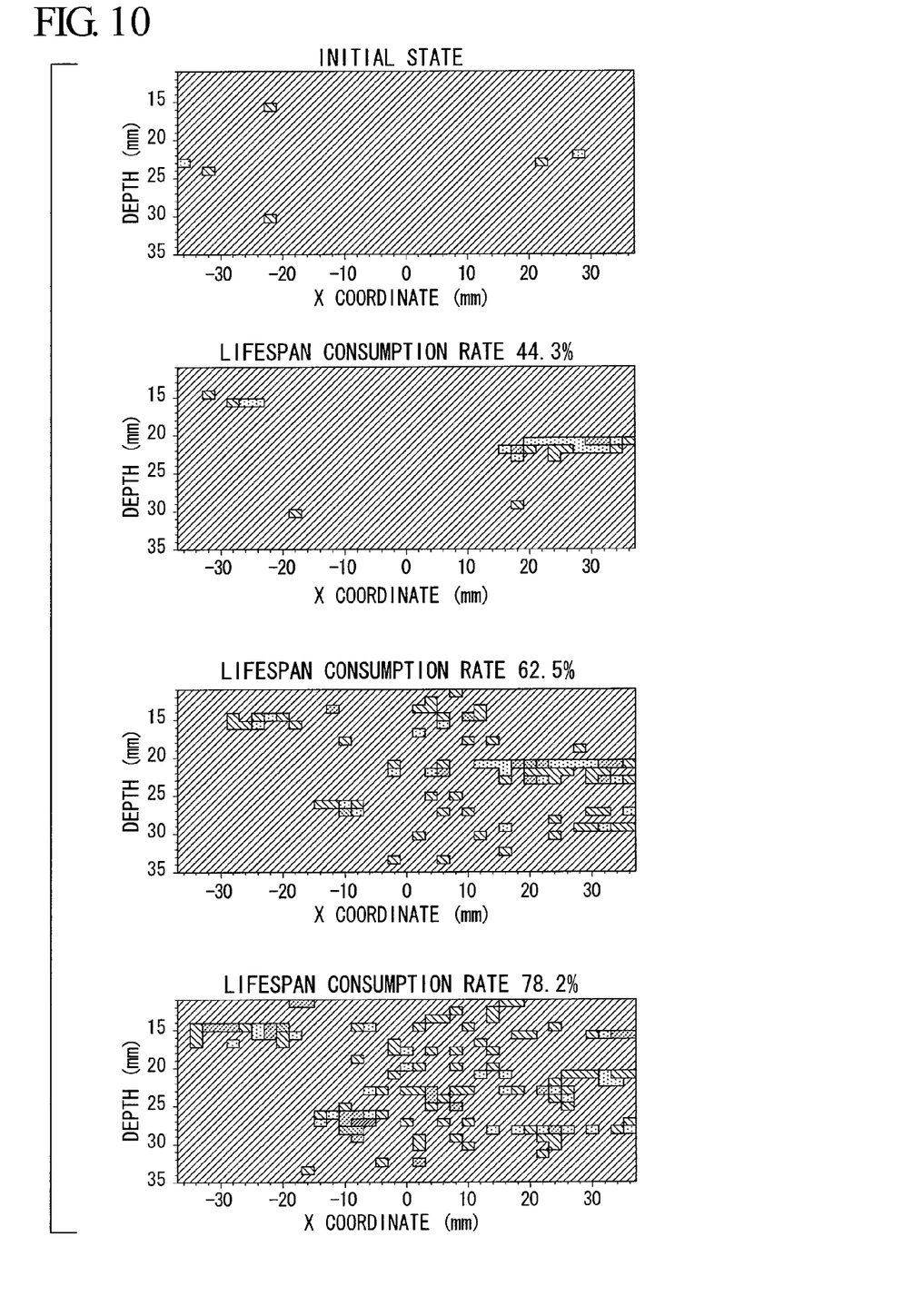
FIG. 10 is a typical view of a defect distribution detected when ultrasonic waves having a frequency bandwidth of 15 to 20 (MHz) are used in the defect inspection apparatus according to an embodiment of the present invention.
Figure 11:
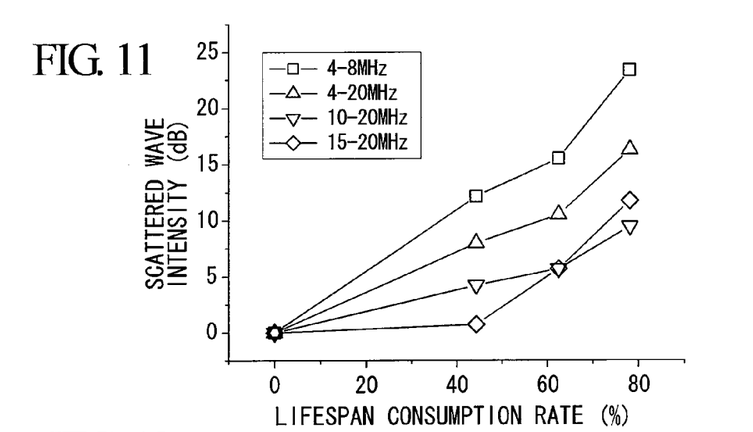
FIG. 11 is a characteristic view showing a relationship between the lifespan consumption rate and parameters showing the scattered wave intensity when ultrasonic waves having a variety of frequency bandwidths are used.

FIG. 7 shows the defect distribution from the point in time when the inspection material R began operating until creep damage (i.e., until the lifespan consumption rate was 100%) when ultrasonic waves having a frequency band of 4 to 8 (MHz) were used. FIG. 8 shows the corresponding defect distribution when ultrasonic waves having a frequency band of 4 to 20 (MHz) were used. FIG. 9 shows the corresponding defect distribution when ultrasonic waves having a frequency band of 10 to 20 (MHz) were used. FIG. 10 shows the corresponding defect distribution when ultrasonic waves having a frequency band of 15 to 20 (MHz) were used. FIG. 11 is a characteristic view showing a relationship between the lifespan consumption rate and parameters showing the scattered wave intensity when ultrasonic waves having the above described respective frequency bands were used.

As is shown in FIG. 7 through FIG. 10, irrespective of the frequency band, it is possible to obtain the same defect distribution as that shown in FIG. 5 in accordance with the rise in the lifespan consumption rate. However, as is shown in FIG. 11, it can be seen that in the case of ultrasonic waves having a frequency band of 10 to 20 (MHz) and those having a frequency band of 15 to 20 (MHz), there is only a small amount of change in the parameters showing the scattered wave intensity for the lifespan consumption rate, and the detection sensitivity of the scattered waves is poor.

In contrast, in the case of ultrasonic waves having a frequency band of 4 to 8 (MHz), it can be seen from FIG. 11 that there is excellent detection sensitivity, however, as is shown in FIG. 7, there is also considerable material noise from outside the areas around the weld portions, and it is difficult to acquire significant noise signals (i.e., noise signals that are generated by defects which are caused by creep damage). Accordingly, in the present embodiment, it is possible to acquire significant noise signals based on these experiment results, so that it was decided to use ultrasonic waves having a frequency band of 4 to 20 (MHz) which also have excellent detection sensitivity towards scattered waves.

As has been described above, according to the present embodiment, it is possible to quantitatively evaluate the distribution of defects generated inside an inspection material R, and the present embodiment is extremely effective when a process from the occurrence of a defect to the failure of the inspection material is being examined.

Note that the present invention is not limited to the above described embodiment and, for example, the variant examples described below may also be considered.

(1) In the above described embodiment, the distribution of defects generated in the interior of an inspection material R is evaluated quantitatively, however, the present invention is not limited to this and it is also possible to employ a structure in which there is provided a function (i.e., a damage lifespan determination device) that predicts the remaining lifespan of the inspection material R based on the results of a defect distribution evaluation of this type. Specifically, as is the case conventionally, it is possible to predict the remaining lifespan from the remaining lifespan curve shown in FIG. 14.

(2) In the above described embodiment, the defect distribution is detected at 1 mm intervals in the thickness direction of the inspection material R, however, the present invention is not limited to this and it is also possible to appropriately modify the defect detection pitch in the thickness direction. However, if the defect detection pitch in the thickness direction is modified, then it is necessary to adjust the frequency of the ultrasonic waves being used and also the time width divisions of the time width Tg in accordance with the modification.

(3) In the above described embodiment, a description is given of a case in which defects that are caused by creep damage are detected, however, the present invention is not limited to this and the present defect inspection apparatus can also be used to detect defects such as voids and cracks and the like that are generated by hydrogen corrosion and other causes.

What is claimed is:

1. A defect inspection apparatus comprising:
an ultrasonic wave probe;
an ultrasonic wave transmitting and receiving device configured to irradiate ultrasonic waves via the ultrasonic wave probe onto a surface of an inspection material on which a predetermined propagation medium has been provided, and to also receive as noise signals, ultrasonic waves that have been scattered by defects present in the interior of the inspection material;
a frequency spectrum calculation device configured to perform time division on the noise signals so as to divide them into time widths that correspond to positions in the depth direction of the inspection material, and calculates a frequency spectrum for each one of the time-divided noise signals; and
a defect distribution detection device configured to calculate values showing a level of defect progression at each of the positions in the thickness direction within the inspection material based on the frequency spectrums.

2. The defect inspection apparatus according to claim 1, further comprising:
an ultrasonic probe drive device that moves the ultrasonic probe along the surface of the inspection material, and also lowers the ultrasonic probe towards this surface so that the ultrasonic probe comes into contact with the surface at each inspection position on the surface of the inspection material, and wherein,
for each of the inspection positions, the defect distribution detection device calculates values showing the level of defect progression corresponding to a position in the depth direction of the inspection material, and creates two-dimensional distribution data for the value which shows the level of defect progression.

3. The defect inspection apparatus according to claim 2, wherein the ultrasonic probe is rotated in an in-plane direction of the inspection surface when it is being brought into contact via the propagation medium with the surface of the inspection material.

4. The defect inspection apparatus according to claim 1, wherein
the ultrasonic wave transmitting and receiving device receives via the ultrasonic wave probe, ultrasonic waves that have been reflected by the bottom surface of the inspection material as bottom surface reflected signals, and wherein
the defect inspection apparatus further comprises:
a determination device that determines whether the ultrasonic waves are being correctly irradiated onto the inspection material based on a strength of the bottom surface reflected signals.

5. The defect inspection apparatus according to claim 1, wherein the frequency of the ultrasonic waves is set in accordance with the time widths which are obtained as a result of time division being performed on the noise signals.

6. The defect inspection apparatus according to claim 1, further comprising a breakage lifespan determination device that determines a lifespan before breakage of the inspection material based on the value showing the level of defect progression.

7. A defect inspection method comprising:
irradiating, using an ultrasonic wave probe, ultrasonic waves onto a surface of an inspection material via a predetermined propagation medium;
detecting, using an ultrasonic wave transmitting and receiving device, ultrasonic waves that have been scattered by defects present in the interior of the inspection material as noise signals;
performing, using a frequency spectrum calculation device performs time division on the detected noise signals so as to divide them into time widths that correspond to positions in the depth direction of the inspection material;
calculating, using the frequency spectrum calculation device, a frequency spectrum for each one of the time-divided noise signals; and
calculating, using a defect distribution detection device, values showing a level of defect progression at each of the positions in the thickness direction within the inspection material based on the frequency spectrums.

8. The defect inspection method according to claim 7, wherein the irradiating step further comprises:
irradiating ultrasonic waves onto each inspection position on the surface of the inspection material; and
the step of calculating using the defect distribution detection device further comprises:
calculating, for each of the inspection positions, values showing the level of defect progression corresponding to a position in the depth direction of the inspection material; and
creating two-dimensional distribution data for the values which show the level of defect progression.

9. The defect inspection method according to claim 7, wherein the propagation medium is oil having a density of 1 (g/cm$^3$) or less and a kinematic viscosity of 100 (mm$^2$/s) or less.

10. The defect inspection method according to claim 7, further comprising:
detecting the ultrasonic waves that have been reflected by the bottom surface of the inspection material as bottom surface reflected signals, and
determining whether the ultrasonic waves are being correctly irradiated onto the inspection material based on a strength of the bottom surface reflected signals.

11. The defect inspection method according to claim 7, wherein the frequency of the ultrasonic waves is set in accordance with the time widths which are obtained as a result of time division being performed on the noise signals.

12. The defect inspection method according to claim 7, further comprising determining a lifespan before breakage of the inspection material based on the value showing the level of defect progression.

* * * * *